United States Patent [19]

Colart

[11] Patent Number: 4,919,423
[45] Date of Patent: Apr. 24, 1990

[54] PSYCHOMOTRICITY TEST-TOY

[76] Inventor: André H. Colart, Chemin des Fermes, Villers sur Trie 60590 Sérifontaine, France

[21] Appl. No.: 271,318

[22] Filed: Jun. 17, 1988

Related U.S. Application Data

[63] Continuation-in-part of Ser. No. 639,137, Aug. 6, 1984, abandoned.

[51] Int. Cl.$^5$ ............................................. A63B 67/14
[52] U.S. Cl. .................................. 273/109; 273/112; 273/113
[58] Field of Search ............... 273/109, 110, 112, 113, 273/115, 116

[56] References Cited

U.S. PATENT DOCUMENTS

| 855,919 | 6/1907 | Wood | 273/112 |
|---|---|---|---|
| 4,089,526 | 5/1978 | Olving | 273/110 |

FOREIGN PATENT DOCUMENTS

| 0103793 | 12/1941 | Sweden | 273/112 |
|---|---|---|---|
| 0011197 | of 1889 | United Kingdom | 273/112 |
| 0011829 | of 1899 | United Kingdom | 273/112 |

OTHER PUBLICATIONS

Schaper Toys Catalog, "Twizzle".

*Primary Examiner*—Edward M. Coven
*Assistant Examiner*—Gary Jackson
*Attorney, Agent, or Firm*—Cushman, Darby & Cushman

[57] ABSTRACT

The invention provides a toy of skill usable as a test for evaluating the psychomotricity of an individual comprising an axis to which and around which is associated at least one curved element forming a track on its inner face extending substantially parallel to said axis, and at least one ball adapted to roll on said track by exerting a rotation of the toy around said axis maintained in a substantially horizontal position.

5 Claims, 2 Drawing Sheets

PSYCHOMOTRICITY TEST-TOY

This is a continuation-in-part of application Ser. No. 06/639,137 filed Aug. 6, 1984, now abandoned deriving from international application No. PCT/FR83/00256 filed Dec. 22, 1983.

BACKGROUND OF THE INVENTION

The present invention refers to a toy of skill usable as a test for evaluating the psychomotricity of an individual, and concerns more particularly a device in which a ball is to run.

A number of devices contained in a box are well known in this field, for instance those which are described in the English Pat. Nos. 11,197 by Michell and No. 11,829 by Carter, and the Swiss Pat. No. 257436 by Bebié.

A number of unboxed devices are also known, for instance the "Twizzle" of Schaper toys (registered trade-mark), the frying-pan-shaped toy described in the U.S. Pat. No. 3,702,191 by Zilius, and the device described in the Swedish Pat. No. 103 793 by Carlsson.

These toys comprise a spiral-wound track, on plan, or on a pyramid, or on a cone, and the ball rolls on this track by exerting alternative tilts of the toys.

Most of these devices may be manipulated with one hand only, and the required movements are slight in amplitude.

SUMMARY OF THE INVENTION

One object of the present invention is to provide a toy more attractive than the previous, and a device for more conclusive psychomotricity tests, by a conformation involving the use of both hands, for movements of large amplitude, with a manipulatory skill and a synchronism both increased in comparison with previous devices.

With this in view, the toy according to the invention comprises an axis to which and around which is associated at least one curved element forming a track on its inner face extending substantially parallel to said axis, and at least one ball adapted to roll on said track by exerting a rotation of the toy around said axis maintained in a substantially horizontal position.

Said curved element is preferably a substantially transparent strip connected to said axis and spiral-wound from and around this axis, this spiral strip having a width extending substantially parallel to said axis, the user following the movement of said ball by looking through said spiral strip.

Said curved element or spiral strip may be formed of a succession of parts substantially flat, substantially parallel to said axis, and joined by curved parts.

Said axis may be formed of a tube opening at least at one of its two extremities and having a wall comprising at least one orifice opening on said track.

According to a preferred embodiment, the toy comprises two flanges pressed against opposite edges of said spiral strip so as to confer on this toy the shape of a box, at least one of the extremities of said axis or tube opening on the outside of one of said flanges.

Said spiral strip may extend with a width narrowing as far as said axis or tube, and may include a medial marking line.

DESCRIPTION OF THE DRAWINGS

The annexed drawings, given as an in no way limitative example, will help to better understand the invention together with the advantages it offers.

DESCRIPTION OF THE PREFERRED EMBODIMENT

Figure 1:
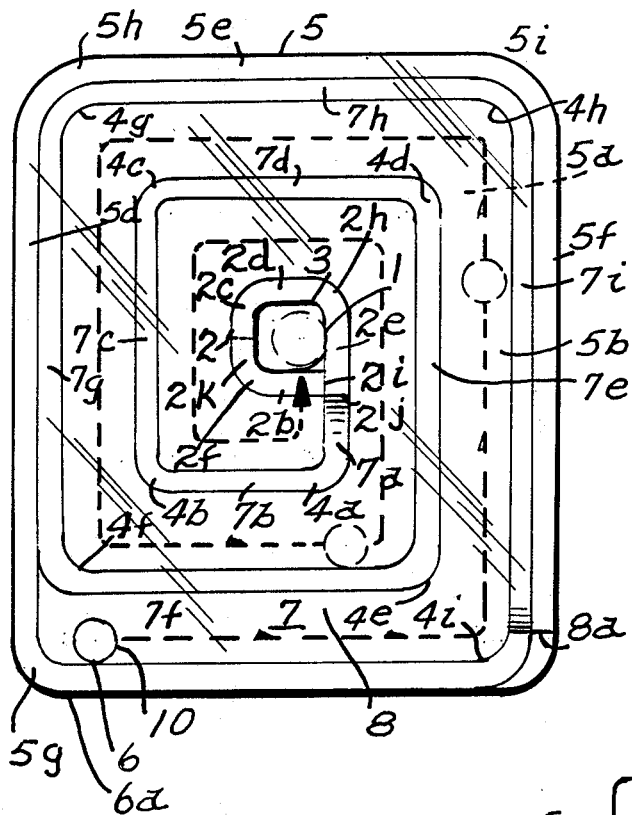
FIG. 1 is a side elevation view of a toy according to the invention.

The toy disclosed in the drawings comprises a transparent strip 8 spiral-wound, two transparent flanges 5a and 5b, and, inside, a ball 10 intended to be metallic, having a diameter about 9 or 10/32 in. (7 or 8 mm).

Figure 2:
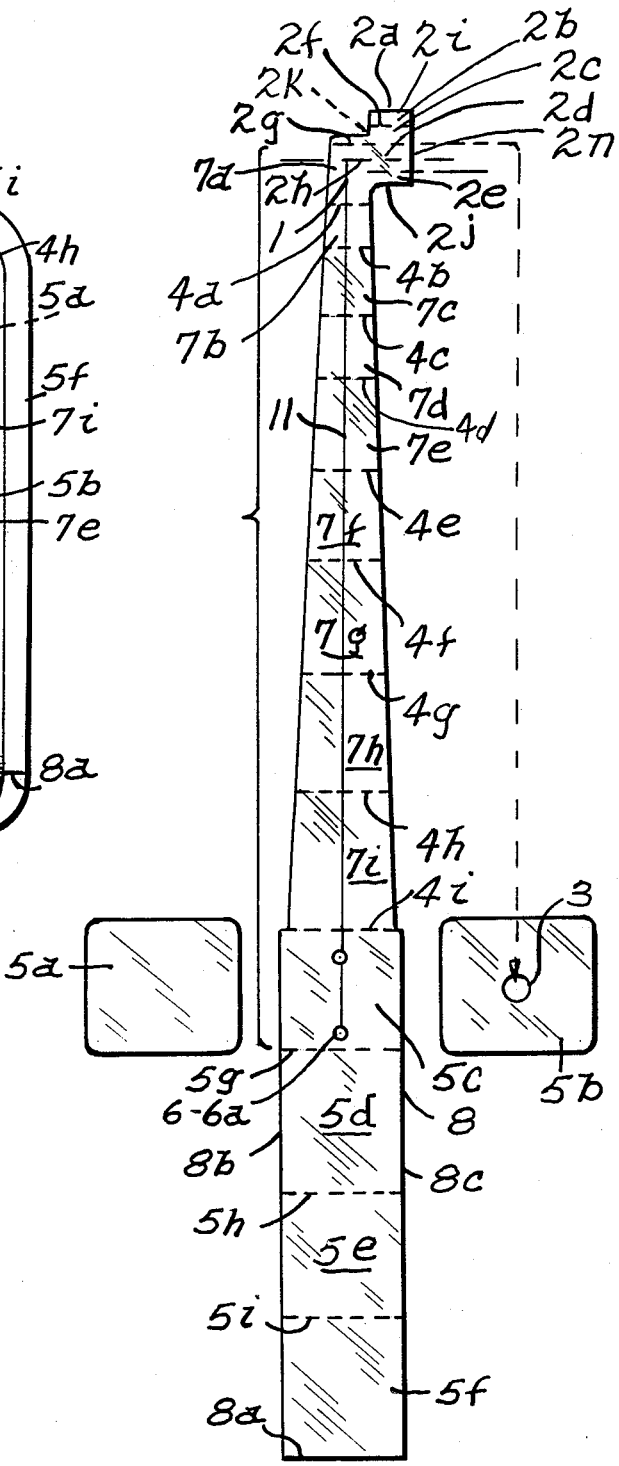
FIG. 2 is a plan, unfolded and exploded view, on a reduced scale, of the same toy.

Strip 8 in unfolded shape and flanges 5a and 5b, shown on plan in FIG. 2, are cut out of a flat sheet of transparent and colourless acrylic resin (methyl polymethacrylate) 5/32 in. (4 mm) thick, registered trademark "Altuglas".

Figure 3:
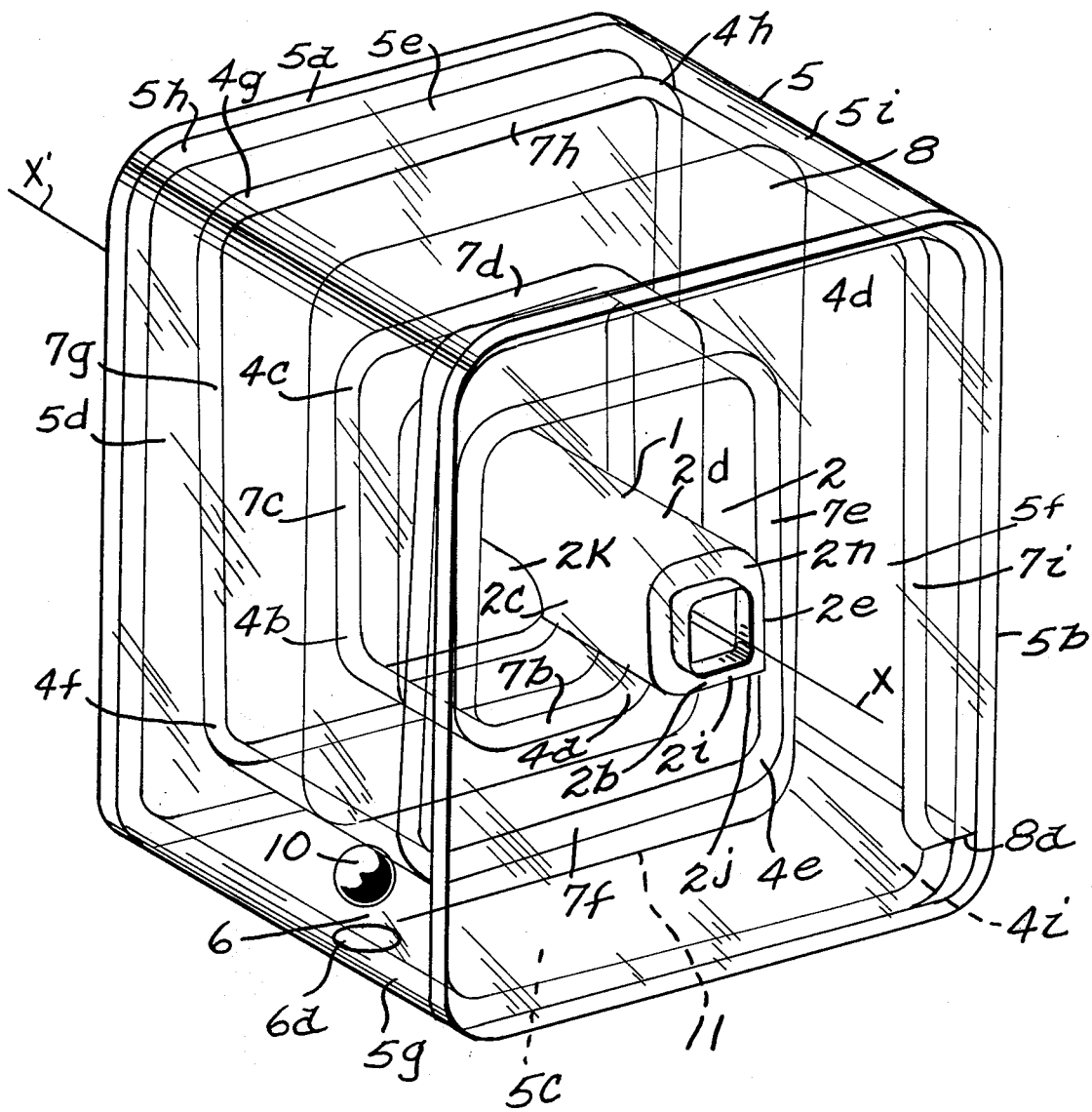
FIG. 3 is a perspective view of the same toy.

FIG. 1 shows, in side elevation, said strip 8 hot wound by successive foldings along tracing in dot-and-dash lines laid in width of this strip in FIG. 2, by means of electric resistors according to the well-known process for acrylic resins in sheets, first to make a tube 2 forming an axis along direction X'X of FIG. 3, and then to make a spiral from and around this tube 2 or axis X'X, in a succession of flat parts 2b to 2e, 7a to 7i, and 5c to 5f, joined at right angles by the curved parts formed by the rounded folds 2f to 2h, 4a to 4i, and 5g to 5i.

The tube 2 is formed by joining the edges 2i and 2j of the protuberance 2a of strip 8 seen top right in FIG. 2, this tube 2 comprising the four flat parts 2b to 2e joined by folds 2f to 2h.

From this fold 2h and around this tube 2 or axis X'X, the inner face of spiral strip 8 forms a track 7, within the part formed by the ten flat parts 7a to 7i and 5c joined by folds 4a to 4i;

whereas the last three flat parts 5d to 5f, joined to said flat part 5c by fold 5g, and joined successively by folds 5h and 5i, are pressed around the spiral in such a way that the extremity 8a of spiral strip 8 coincides with said fold 4i, to form a close turn 5c to 5f which is the outer turn of said spiral strip 8;

said track 7 thus extending by two turns and a half between fold 2h delimiting a central extremity 1, and fold 5g delimiting a peripheral extremity provided with a starting-point 6 for ball 10, marked by means of a round point 6a close upon said fold 5g on the outer face of flat part 5c.

The edges 2i and 2j and every said folds are parallel each other, in such a way that these folds and every said flat parts extend parallel to tube 2 or axis X'X, and that the spiral strip 8, and specially the track 7, has a width extending parallel to said tube 2 or axis X'X, according to the invention.

Flanges 5a and 5b are pressed against the opposite edges 8b and 8c of spiral strip 8, on the outer turn 5c to 5f, by means of gluing or welding, in such a way as to confer on the toy the shape of a transparent and substantially cubical box 5, with edges about 4 in. (10 cm) long, enclosing said track 7, tube 2, and ball 10; said flanges 5a and 5b forming side faces of box 5, and said flat part 5c being common to track 7 and box 5.

In FIG. 1, spiral strip 8 is seen by transparency through flange 5b.

At its junction with flat part 7a, comprising the central extremity 1 of track 7, tube 2 bears in its wall 2b-2c a cutting out forming an orifice 2k opening on said track 7.

Opposite to this orifice 2k, the extremity 2n of said tube 2 opens outside flange 5b through a hole 3 pierced in this flange, and is brought together with the edge of this hole 3 by means of gluing or welding.

The point of the game consists in causing ball 10 to roll on track 7 between the turns of spiral strip 8, on principle from starting-point 6 to central extremity 1, substantially along a median marking line 11 povided on the outer face of spiral strip 8 to help the user guiding ball 10, as shown by circles and arrows in dotted lines in FIG. 1 and 2.

Exerting a rotation of the toy on itself around tube 2 or axis X'X, while trying to maintain this tube or axis in a horizontal position, in order that the width of strip 8, and track 7, be horizontal when ball 10 passes, to avoid this ball deviating toward one or another of opposite edges 8b and 8c of strip 8, and while maintaining said tube 2 or axis X'X in a plane facing the user, in order that said width of strip 8 presents itself facing him so that he can control and correct the position of ball 10 in relation to said opposite edges 8b and 8c by looking at this ball by transparency through the turns of said strip 8 and by exerting some side tilts of the toy;

bear in mind that, inside box 5, spiral strip 8 extends with a width narrowing as far as tube 2, in such a way that said opposite edges 8b and 8c of strip 8 are recessed inward with respect to flanges 5a and 5b, which forms between these flanges and said edges 8b and 8c a gap through which ball 10 falls from track 7, but remains captive within box 5,if this ball reaches one or other of said opposite edges 8b and 8c before reaching central extremity 1, in which case it is necessary to start the game again from starting-point 6; it being understood that on the other hand it is more and more difficult to keep ball 10 on track 7 as it comes nearer central extremity 1;

the main difficulty arising from some jolts caused by the fact that said rotation, by two turns and a half, must be exerted by taking the toy alternately in the left hand and the right hand; the user's fingers being placed on the outer turns 5c to 5f of spiral strip 8, whereas the flanges 5a and 5b come facing the palms of the hands.

During this rotation, the ball comes and wedges itself in each fold it meets and is drawn with this fold for a quarter turn tending to bring this ball back toward the point it came from, after which this ball breaks away from said fold and crosses the following flat part in the opposite direction to the rotation of the toy to come and wedge itself in the following fold, and so on.

In this way, it is in reality the strip 8, and track 7, that passes beneath the ball, while this ball, while remaining under tube 2 and while being animated by a to and fro motion in relation to the user, climbs up from flat part to flat part toward central extremity 1.

The number of folds traversed by the ball gives the measure of the performances and psychomotricity of the user.

If the ball reaches said extremity 1, it is enough to incline the toy toward tube 2 to cause said ball enter it through orifice 2k and to leave box 5 through hole 3; this ball being then picked up in the hand.

To put this ball back into play, it is necessary to reintroduce it in box 5 through hole 3 and tube 2.

It is also possible to play in the opposite direction from the foregoing, to bring the ball back from central extremity 1 or from any point on the track as far as starting-point 6.

The toy according to the invention may be used for leisure activities, but also for professional purposes, as a measuring appliance for psychomotricial capacities, for instance for air pilots, figure skaters, musicians, surgeons, and others; bearing in mind that it offers improvement in the capacities of the users in all cases.

The embodiment above described enables the invention to be well understood and it is thus that the prototype was executed; however it is quite obvious that the invention is not limited to the described and represented embodiment, nor to the dimensions indicated.

In particular, the toy according to the invention and specially the spiral strip can be produced by injection molding rather than by cutting and folding, and the box can have various forms, as for instance spherical or cylindrical or taking the shape of a fruit, an animal's head, or others.

What is claimed:

1. A toy of skill usable as a test for evaluating the psychomotricity of an individual comprising an axis to which and around which is associated at least one curved element forming a track on its inner face extending substantially parallel to said axis, and at least one ball adapted to roll on said track by exerting a rotation of the toy around said axis maintained in a substantially horizontal position; said curved element being formed from a continuous strip having portions which are substantially flat and formed to be substantially parallel to said axis with adjacent said flat portions having between them a curved portion.

2. A toy according to claim 1 made by injection molding.

3. A toy of skill usable as a test for evaluating the psychomotricity of an individual comprising an axis to which and around which is associated at least one curved element forming a track on its inner face extending substantially parallel to said axis, and at least one ball adapted to roll on said track by exerting a rotation of the toy around said axis maintained in a substantially horizontal position, said curved element being a substantially transparent strip connected to said axis and spiral-wound from and around said axis, said spiral strip having a width extending substantially parallel to said axis, whereby an individual may observe the movement of the ball by looking through said spiral strip, said axis being formed of a tube opening at least at one of its two extremities and having a wall comprising at least one orifice opening on said track.

4. A toy of skill usable as a test for evaluating the psychomotricity of an individual comprising an axis to which and around which is associated at least one curved element forming a track on its inner face extending substantially parallel to said axis, and at least one ball adapted to roll on said track by exerting a rotation of the toy around said axis maintained in a substantially horizontal position, said curved element being a substantially transparent strip connected to said axis and spiral-wound from around said axis, said spiral strip having a width extending substantially parallel to said axis, whereby an individual may observe the movement of the ball by looking through said spiral strip, said axis being formed of a tube, said toy comprising two flanges pressed against opposite edges of said spiral strip so as to confer on said toy the shape of a box, at least one of the extremities of said axis opening on the outside of one of said flanges.

5. A toy of skill usable as a test for evaluating the psychomotricity of an individual comprising an axis to which and around which is associated at least one curved element forming a track on its inner face extending substantially prallel to said axis, and at least one ball adapted to roll on said track by exerting a rotation of the toy around said axis maintained in a substantially horizontal position, said curved element being a substantially transparent strip connected to said axis and spiral-wound from around said axis, said spiral strip having a width extending substantially parallel to said axis, whereby an individual may observe the movement of the ball by looking through said spiral strip, said axis being formed of a tube opening at least one of its two extremities and having a wall comprising at least one orifice opening on said track, said strip extending with a width narrowing as far as said axis and including a medical marking line.

* * * * *